(12) United States Patent
Aguilar Rubido et al.

(10) Patent No.: US 6,355,414 B1
(45) Date of Patent: Mar. 12, 2002

(54) IMMUNOPOTENTIATING FORMULATIONS FOR VACCINAL USE

(75) Inventors: Julio Cesar Aguilar Rubido; Verena Lucila Muzio Gonzalez; Maria de Jesus Leal Angulo; Gerardo Enrique Guillen Nieto; Eduardo Penton Arias; Gloria Veliz Rios; Dagmara Pichardo Diaz; Antonieta Herrera Buch; Enrique Iglesias Perez; Luis Javier Cruz Ricondo; Tania Carmenate Portilla; Cirse Mesa Pardillo; Maydel Hechavarria Gay; Maylin Diaz Martinez; Juan Joel Madrazo Piñol, all of Havana (CU)

(73) Assignee: Centro de Ingenieria Genetica y Biotechnologia, Havana (CU)

(*) Notice: Subject to any disclaimer, the term of this patent is extended or adjusted under 35 U.S.C. 154(b) by 0 days.

(21) Appl. No.: 09/380,790
(22) PCT Filed: Mar. 5, 1998
(86) PCT No.: PCT/CU98/00003
§ 371 Date: Jan. 6, 2000
§ 102(e) Date: Jan. 6, 2000
(87) PCT Pub. No.: WO98/39032
PCT Pub. Date: Sep. 11, 1998

(30) Foreign Application Priority Data

Mar. 6, 1997 (CU) .................................................. 27/97

(51) Int. Cl.[7] .................................................. C12Q 1/70
(52) U.S. Cl. .............................. 435/5; 514/54; 514/885; 424/278.1
(58) Field of Search .......................... 424/278.1; 435/5; 514/54, 885

(56) References Cited

U.S. PATENT DOCUMENTS 5,308,838 A * 5/1994 McAnalley et al. .......... 514/54

FOREIGN PATENT DOCUMENTS

EP 0659768 A2 * 5/1994

OTHER PUBLICATIONS

Fogleman et al (Veterinary And Human Toxicology, Apr. 1992, vol. 34, pp. 144–147, abstract only).*

* cited by examiner

Primary Examiner—Ali R. Salimi
(74) Attorney, Agent, or Firm—Hoffmann & Baron, LLP

(57) ABSTRACT

The present invention is related to the field of medicine, particularly to the use of new adjuvant formulations with vaccine antigens. The technical objective pursued with this invention is, precisely, the development of formulations that are able to increase and/or modulate the immune response of the organism to vaccine antigens in the serum and the mucous lining. With this aim, a formulation was developed that contained as the main components the surface antigen of the hepatitis B virus and the acemannan in adequate proportions. As an extension of this result, formulations were developed in which a) HBsAg was used as the homologous or heterologous antigen carrier b) delivery systems of particulated antigens and c) soluble antigens, combined with the acemannan in specific proportions. The formulations of this invention are applicable in the pharmaceutical industry as vaccine formulations for human and veterinary use.

15 Claims, 8 Drawing Sheets

| Grupos | 1 | 2 | 3 | 4 | 5 |
|---|---|---|---|---|---|
| Composition | Ag 5μg | Ag 5μg | Ag 5μg | Ag 5μg | Ag 5μg |
| | PBS | PS 1.5 mg/mL | PS 3 mg/mL | PS 6 mg/mL | PS 9 mg/mL |
| G (UI/L) | 43 | 897 | 1300 | 1632 | 276 |
| Ln (G) | 3.75 | 6.8 | 7.17 | 7.4 | 5.62 |
| Ln (Low. lim.) | 3.13 | 6.05 | 6.39 | 7.05 | 4.78 |
| Ln (Upp. lim.) | 4.38 | 7.55 | 7.95 | 7.75 | 6.46 |

Extraction day 26

| Groups | G1 | G2 | G3 | G4 | G5 |
|---|---|---|---|---|---|
| Composition | Ag 2µg PS 6mg/mL | Ag 10µg PS 6mg/mL | Ag 20µg PS 6mg/mL | Ag 2µg Alum 0.5mg/mL | Ag 10µg CT 1µg/dosis |
| Ln (G) | 9.33 | 11.27 | 12.45 | 9.74 | 12.28 |
| Ln (Low. lim.) | 9.1 | 10.86 | 12.23 | 9.48 | 12.12 |
| Ln (Upp. lim.) | 9.57 | 11.69 | 12.67 | 10.02 | 12.45 |

Extraction day 42

| Groups | G1 | G2 | G3 | G4 | G5 |
|---|---|---|---|---|---|
| Ln (G) | 12.02 | 14.35 | 15.23 | 12.75 | 13.86 |
| Ln (Low. lim.) | 11.53 | 13.97 | 14.97 | 12.44 | 13.6 |
| Ln (Upp. lim.) | 12.51 | 14.72 | 15.5 | 13.06 | 14.12 |

Extraction day 70

| Groups | G1 | G2 | G3 | G4 | G5 |
|---|---|---|---|---|---|
| Ln (G) | 14.51 | 15.4 | 15.41 | 13.68 | 14.85 |
| Ln (Low. Lim.) | 14.28 | 15.3 | 15.37 | 13.48 | 14.72 |
| Ln (Upp. Lim.) | 14.73 | 15.5 | 15.45 | 13.88 | 14.98 |

|  | G1 | G2 | G3 | G4 | G5 |
|---|---|---|---|---|---|
| Ln (G(UR)) | 5.87 | 7.66 | 6.77 | n.s. | 6.49 |
| Ln (Low. lim.) | 5.04 | 6.94 | 6.10 | n.s. | 5.98 |
| Ln (Upp. lim.) | 6.71 | 8.38 | 7.44 | n.s. | 7.00 |

IMMUNOPOTENTIATING FORMULATIONS FOR VACCINAL USE

This application is the U.S. National Phase of International Application Number PCT/CU98/00003 filed Mar. 5, 1998.

BACKGROUND OF THE INVENTION

The present invention is related to the field of medicine, particularly to the development of new formulations for immunological potentiation allowing the increase of the amount and quality of the immune response to vaccine antigens.

The technical aim of the invention is the development of formulations that are capable of increasing the levels of the immune response of the body to vaccine antigens.

The adjuvants are substances that increase or optimize the immune response to antigens inoculated through the mucosal or systemic routes. The adjuvants or their formulations are combined with the antigen to generate or potentiate the type of response desired, decrease the number of inoculations and reduce the amount of antigen needed to obtain and maintain protection (McElrath, M. C. 1995 Seminars in Cancer Biology 6: 375–385).

Adjuvants have been developed as a necessity due to the advancements of modern biotechnology with the production of pure soluble recombinant and synthetic antigens. In general, these antigens are safe, but generally shows a decreased immunogenicity compared to those of the original organism. An important function of adjuvants or their formulations, is to increase the complexity of the antigen facing the immune system, in a safe way, thus increasing its immunogenicity (Alving, R. C. 1992 AIDS Res. Hum. Retroviruses 8 (8): 1427–1430).

At present, the search for new adjuvants and immunological stimulators, as well as the development of new ways of delivering antigens and pharmaceuticals, is one of the lines of world research in the pharmaceutical field, especially in vaccines. The development of the adjuvants for mucosal use is a present need in the vaccine field (Report of the Expert Panel VI: Concerted efforts in the field of mucosal immunology 1996 Vaccine 14: 644–664). They may be classified as mucosal and systemic adjuvants, considering that the physiological characteristics on receiving and processing the antigen in both inoculation routes generate different adjuvation procedures. The mucosal route, according to the characteristics of the antigen, require binding or coating procedures with specific ligands that send the antigens to the M cells. The adjuvant activity for mucosal antigens is obtained through strategies that help the antigen to cross the borders imposed by the route. The physical characteristics of the antigen may favor its phagocytosis. Once the antigen has been assimilated, the adjuvant may influence the response by any of the known mechanisms: antigen adsorption, depot effect, cytokine induction, complement activation, recruiting of different cell populations of the immunological system, antigen delivery to different antigen presenting cells, regulation of the expression through class I or class II and the stimulation to produce different antibody subtypes (McElrath M. C. 1995 Seminars in Cancer Biology 6: 375–385).

Some of the immunological stimulators known, as muramyldipeptides (MDP), monophosphoryl-lipid A (MPL), the lipoid amine Avridine and those known as toxins: *V. cholerae* (CT) and of *E. coli* (HLT) toxins, are recognized adjuvants for antigens administered through the mucous route (Walker, R. I. 1994 Vaccine 12 (5): 387–400).

The MDP and MPL have been studied in liposomal formulations for therapeutic and prophylactic use, however, the toxins and their sub-units (specially the CT and CTB) are the most common mucosal adjuvants.

The ability of CT to act as an oral adjuvant has been confirmed by a large number of researchers (McGhee, J. R. et al. 1992 Vaccine 10 (2): 75–88). The Cholera Toxin does not fulfill the classical definition of an adjuvant because it stimulates an immune response against itself and its adjuvant activity depends on its immunogenicity (Elson, C. O. 1987 Fed. Proc. 46: 1778). The immunomodulating effects of the CT and HLT explaining their strong adjuvant activity, include the increase in antigen presentation by several types of B cells, the increase in B cells differentiation to the IgA isotype, the interaction with T cells and the induction of cytokine production (Lintermans, P. 1995 Advanced Drug Delivery Reviews 18: 73–89).

From the practical point of view, the use of the holotoxin in man is not possible due to its toxicity. A better strategy is the detoxification of the CT, by separating the CTA subunit or through mutations of the gene codifying it. CT as well as the CTB (less toxic subunit of CT) may potentiate the immune response to several antigens bound covalently through specific interactions with M cells (Holmgren, J. et al. 1993 Vaccine 11: 1179–1184).

The antigen delivery systems have reached a sufficiently high degree of development as to have an impact on immunization. It is expected that the solid particulated systems for parenteral or non-parenteral administration should be among the first licensed products (Li Wan Po et al. 1995 Advanced Drug Delivery Reviews 18: 101–109).

Through the possibilities offered by the antigen delivery systems in the particulation of soluble antigens, and taking advantage of the physiological characteristics of the mucosal route, these systems have been tested and have shown adjuvant activity. In the literature they have been classified as:

a) synthetic/inactivated and b) alive (Report of the Expert Panel VII: Vaccine Delivery Systems 1996 Vaccine 14: 644–664). Enclosed in the first group, according to their non-living characteristic, there are two different groups. In respect to the first group, the artificial polymeric particles have been studied with different results comprising: the co-polymeric microspheres of lactic and glycolic acids, also alternative polymers as polyphosphacenes, cellulose acetate polymers, iminocarbonates, ethylenvinyl acetate polymers, proteinoid microspheres, dextran polyanhydrid and nanospheres; the particles produced from natural materials: alginates, gelatins and seeds of plants and also the liposomes and their variants: proteoliposomes, virosomes and ISCOMs (Li Wan Po et al. 1995 Advanced Drug Delivery Reviews 18: 101–109).

The size of the particles is within the group of important factors for antigen sending. In the case of the mucosal immunization route it has been reported that particles of a diameter greater than 10 $\mu$m are not absorbed (Eldridge J. H. 1990 J. Control. Release 11:205–214). In experiments with rats it was observed that after oral administration, only particles of 5 $\mu$m deeply penetrated the Peyer Patches and those of 1 $\mu$m of diameter, penetrated the lymphonodes and went into the bloodstream (Jani, P. et al 1990 J. Pharm. Pharmacol. 42:821–826)(Alpar, H. O. et al. 1989 J. Pharm. Pharmacol 41:194–196).

The extrapolation of these results in man is not yet defined and sometimes the adsorption by the gastrointestinal tract is not a requirement for adjuvant activity although it has been proven that with the adsorption of the diphtheria toxoid in plant seed of up to 2 mm diameter, the immune response was potentiated (Mirchamski, H. et al. 1994 Vaccine 12:1167–1172).

The determination of the optimum size of the controlled release systems through the oral, rectal or vaginal routes is under study (Li Wan Po et al. 1995 Advanced Drug Delivery Reviews 18:101–109).

Another factor affecting the particles is the hydrophobic-hydrophilic balance, which may be modified to obtain a modulation of the immune response (Jani, P. et al 1990 J. Pharm. Pharmacol. 42:821–826).

Recently, the use of vaccines of protein cochleates described in 1975 (Papahadjopoulos D. et al 1975 Biochem. Biophys. Acta 394: 483), has been patented. The cochleates are complexes of liposomes and divalent cations (mainly calcium) that, through the calcium-phospholipid interaction, enable the formation of a liposome structure coiled on itself, allowing the immunization through different routes (Gould Foguerite, S. WO 95/09648). With this structure, the immune response of antibodies, as well as the cell mediated responses are stimulated (Gould Foguerite, S. 1994 AIDS Res. Hum. Retroviruses 10 (Supl. 2): S99–S103).

The absorption and passage of the antigens through specialized cells of the epithelium associated to the lymphoid follicle, the M cells is a critical step in the generation of an immune response through the simple intestinal epithelium, which is generally accepted by all authors. Through this process, the antigens are sent to the basal pocket of the M cells, constituting the first contact of the antigen (practically undegraded) with B and T cells and macrophages. The main function of the pocket is to provide the organism with an environment protected from the modulator influence of the external humoral factors (Neutra, R. M. 1996 Annu. Rev. Immunol. 14: 275–300).

In the respiratory tract, the epithelium varies from pseudostratified, to simple. In the bronchi, the simple epithelial zone, the intercellular spaces are sealed by tight binds and the main mechanism for the antigens to enter is through the M cells. At the tonsils, the predominant epithelium is the stratified epithelium. Here, the absorption mechanism of the antigen is closely associated to a net of macrophages and mobile dendritical cells from the bone marrow, of up to 700 cells per $mm^2$. These cells are able to migrate to the organized lymphoid tissue associated to the mucous (O-MALT) or to a lymphonode, presenting the processed antigen that was phagocyted at the surface of the tonsils. Under normal conditions this constitutes the main mechanism for the presentation of the antigens through MHC class II of the respiratory tract (Neutra, R. M. 1996 Annu. Rev. Immunol. 14: 275–300).

The difference in the absorption of the antigen at the oral and nasopharyngeal levels allows to understand why the inoculation of an adjuvant through both routes will not necessarily produce the same results. Therefore, it is not obvious that an adjuvant that is effective through the oral route, will or will not be effective by the nasopharyngeal route. The adjuvants may have different effects in different mucous sites, since different mucous surfaces have different micro-environments. The progress in the knowledge of the physiology of the mucous and the mode of adjuvants action may help to the development of more effective mucosal vaccines. As well as the characteristics of the antigen as: size, presence of mucosal ligands, electric charge, lipophilicity and T dependence may also affect the immune response. (Report of the Expert Panel VI: Concerted efforts in the field of mucosal immunology 1996 Vaccine 14: 644–664). At the same time, other elements of the organism as the hormonal fluctuations during the menstrual cycle, affect the assimilation of the antigen at the vagina. This fact shows the strong collaboration between the dendritic and epithelial cells and explains the variation in the effectiveness of the vaccines through the vaginal route (Parr, E. L.,Parr, M. B. 1992 Vaccine Res. 1: 221–25).

For the case of the simple epithelial route of the intestine, the delivery of non-living vaccines to the M cells has been difficult, given the fact that the unprotected macromolecules are readily digested or dragged by the secretions and the motility of the gastrointestinal tract. There is little information available in relation to the components of the apical membrane of the M cells that may serve as receptors. The liposomes and the micro-particles may adhere to the mucous surfaces by hydrophobic interactions, but the entrance of the antigens to the M cells is inefficient since they are rapidly trapped in the mucous gels and many do not reach the mucous. The macromolecules or particles conjugated or coated with ligands as the CTB, have the limiting factor of their access to the receptors (Neutra, R. M. 1996 Cell 86: 345–348).

Recent experiments in mice, using 28.8 nm coloidal gold particles coated with CTB showed that they were able to adhere and penetrate selectively in M cells of the epithelium associated to the mucous follicle, being unable to penetrate the enterocytes of the so-called "brush border". Larger particles; of approximately 1.13 μm; also coated with CTB, were unable to adhere to M cells, while CTB-FITC particles of approximately 6.4 nm, adhered and entered through both cell types. This experiment demonstrated the role of the glycocalix in the adherence and entering of the antigens through the M cells. The B subunit of the cholera toxin has receptors both in the enterocytes as in the M cells. The use of the ligands bound to particles may result in a specific adherence to M cells, but only in a range of sizes restricted by the glycocalix. Particles of 1 μm or greater, require ligands that are specifically directed to components of the M cells. The identification of these components is still under study (Frei, A. et.al. 1996 J. Exp. Med. 184: 1045–1059).

A group of pathogenic bacteria is able to bypass the difficulties of the non-living systems on being efficiently assimilated by the lack of receptors at the M cells. These bacteria exploit this mechanism to infect mucosal tissues and disseminate themselves systemically before being detained by the immune system. The bacterial pathogens that adhere to the surface of the M cells start the signal transduction events at the epithelial level that promote their entrance. The best known one is the attenuated bacterial strains of *S. typhi* ty21a, for which a lectin type interaction with a receptor of polysaccharidic nature exist on the cell membrane of M cells. Also safe and effective are the attenuated live strains of *V. cholerae* and polio virus for oral immunization. The genetically manipulated strains of these microorganisms were first used in man as carriers of heterologous antigens (Mekalanos, J. J. 1992 Adv. Exper. Med. Biol. New York Plenum Press: 43–50).

The biology of these live vectors introduce new challenges. The vaccine strains of *V. cholerae,* that have no genes for the toxin, may still produce diarrhea, seemingly because the epithelial cells release cytokines as a response to bacterial adherence (Mekalanos, J. J. 1992 Adv. Exper. Med. Biol. New York Plenum Press: 43–50). The main challenge in the use of the genetically manipulated strains of the *S. typhi* and *S. typhimurium* consist in obtaining a sufficient attenuation offering safety while still adhering to the M cells and their proliferation in mucosal tissues, to maintain their immunogenicity. The attenuated strains of Shigella, are also internalized by the M cells, but they have lost their ability to disseminate from cell to cell. This phenomenon is the basis of the attenuation, but there is still a release of local cytokines and chemotactic factors that may cause the rupture of the normal function of the epithelial barrier (Sansonetti, P. J. 1991 Rev. Infect. Dis. 13: 285–292).

The viruses are also studied. The fact that the poliovirus type 1 and the attenuated strain of Sabin use the M cells to cross the epithelial barrier, make them important candidates for oral vaccines to send foreign antigens in man. Vaccinia and other poxviruses are assimilated by mucosal surfaces but their interaction with the M cells is still unknown (Report of the Expert Panel VI: Concerted efforts in the field of mucosal immunology 1996 Vaccine 14: 644–664).

Many complex carbohydrates of natural origin stimulate the cells of the immune system and the reticulum-endothelium system (Davis, S. E. 1975 Am. Chem. Soc. Sympos. Series 15, Jeanes A. Hodge J. Eds. Am. Chem. Soc. Washington D.C.). Among these are the polymers of plants and fungi as the glucans, dextrans and lentinans, all of which are glucose polymers, and the mannans, among which are found the glucomannans and the galactomannans. Also found are the levans and xylans (Tizard, I. R. et al. 1989 Mol. Biother 1:290–296). The activity of many of these polyglycans on macrophages (having glucan and mannan receptors) include the induction of phagocytosis and the secretion of cytokines, leucotriens and prostaglandines. The lentinan, a glucan that is common in mushrooms, stimulates the cell and antibody response in sheep eythrocytes while levan is mytogenic for B cells and a macrophage activator (Simon, P. M. 1994 Exp. Opin. Invest. Drugs 3 (3):223–239).

The acemannan is a mannan composed of mannose with O acetylations in approximately 8 out of every 10 hexose-rests. It is extracted as a major component of the mucilaginous substance or gel of the *Aloe barbadensis* Miller leaf, medicinal plant used throughout history. Different tests in vitro indicate that the manans activate the monocytes and macrophages inducing the production of interferon-γ, factor-α of tumoral necrosis, colony stimulator factor of monocytes and granulocytes, IL-1β and IL-6 (Peng, S. Y. et al. 1991 Mol.Biother. 3: 79–87). The acemannan potentiates the generation of cytotoxic T lymphocytes (CTL) (Womble, D. et al. 1988 Int. J. Immuno-pharmacol. 10:967–974), the cytotoxic activity of Natural Killer (NK) cells (Marshall G. D. et al. 1993 J. Immunol. (part II) 150: Abstr 1381), and also, slightly, the in vitro human alloresponse.

The increase of the cytotoxic activity and the secretion of γ interferon supports the antiviral and antitumoral therapeutic use of acemannan. Its antiretroviral activity was evidenced in animals in the case of feline leukemia (Sheets, M. A. et al. 1991 Mol. Biother. 3: 41–45). Clinical assays in AIDS and cancer patients are currently in course.

Patents have recently been applied in relation to the use of the acemanan as an adjuvant for vaccines. (McAnalley, B. H. EP 0 619 117 A2, Nordgrem, R. M. WO 93/14195), but in none of the two cases the nasopharyngeal use of the acemannanis protected. In both patents the antigens are inoculated by the systemic route (subcutaneous and intramuscular). In relation to the mucosal route, the first patent shows poor results in the oral use of a acemannan formulation. The results obtained with an acemannan oral formulation (shown in the first patent) may be considered poor compared to those obtained by the systemic inoculation route. As previously explained, the adjuvants may have different effects in the different mucous sites due to the physiology of the assimilation of the antigen and the different environment in each route, that may affect the activity of the immunological potentiator (Report of the Expert Panel VI: Concerted efforts in the field of mucosal immunology 1996 Vaccine 14: 644–664). Besides the differences between the mucosal routes, different results have also been obtained when the same adjuvant is used systemically or through mucosal routes. This is the case of the most common systemic adjuvant used, the aluminum hydroxide. This adjuvant has not been more effective than the PBS when mice are inoculated through the oral and nasal routes with antigens for which it is the traditional adjuvant for systemic use—as for example the tetanus toxoid—(Alpar H. O. et al. 1992 Int. J. of Pharm. 88: 335–344). Therefore, it is not obvious that a systemic adjuvant is also necessarily a mucosal adjuvant.

None of the compositions referred in a patent application of a combined vaccine composition containing HBVs antigen contains acemannan and they haven't been used them through the nasopharyngeal route of inoculation (Tyrrell, A. et al. WO 93/24148).

The main technical feature of a patent about the fusion of proteins to LTB to use those fusion proteins as therapeutic and preventive vaccines differs from our main technical feature cause in the description of the preferred embodiments it is stated that the fused protein comprises heat-labile enterotoxin B subunit (LTB) and a protein which is heterologous to heat-labile enterotoxin. The heterologous protein includes, for example, antigens (proteins or polypeptides). In the scope of our claims we consider that this kind of formulations do not meet the characteristics of our formulations (F. Yukio EPA 0 418 626 A2) cause the antigens to be fused in our preparations do not contain as a result of this fusion the adjuvant as a fused protein and to be used it should be mixed with the acemannan.

A lot of articles in the art discuss strategies of delivery to mucosal tissues for antigens in liposomes. These liposomes are immunogenic in mice and guinea pigs at a low dose and without any other adjuvant (Ilona Idänpään-Heikkilä et al. Vaccine 13 (16), 1995: 1501–1508);(Daiichi pharm co. LTD, Database WPI, AN 96-379257). Other antigen delivery systems has been used (M, Yukata et al. DE 196 27 392 A1). Our work consider the mixture of soluble proteins delivered in antigen delivery systems with acemannan as a way to increase the immune response until levels achieved throught systemic inoculations.

SUMMARY OF THE INVENTION

The present invention is related to a vaccine formulation for nasopharyngeal administration, having as its main components subunit particulated antigens and the acemannan, in adequate proportions.

DISCLOSE OF THE INVENTION

Figure 1:
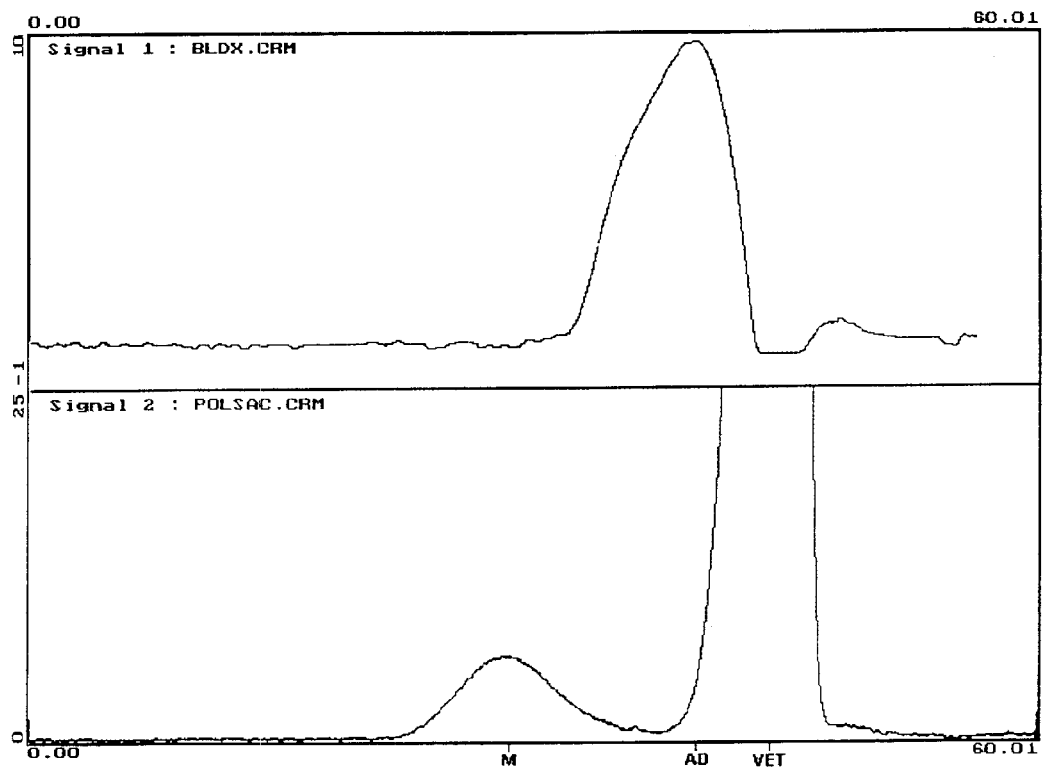
FIG. 1. HPLC Chromatography. AD: Dextran blue (2,000 kDa), M: sample, VET: Total elution volume. Chromatographic processor BioCROM Version 2.3 (1994). Detector: Refraction index (Knauer). Gel: TSK G6000PW (Fractionation range: 500–50,000 kDa). Dimensions: 7.5× 600 mm. Flow rate: 0.5 ml/min. Buffer: PBS. Volume of sample applied; 100 µl.

The present invention is related to a vaccine formulation for nasopharyngeal administration, having as its main components subunit particulated antigens and the acemannan, in adequate proportions.

The novelty of this invention is due to the properties resulting from its nasopharyngeal administration, these are: to generate a systemic immunity of similar intensity and higher quality for similar antigen doses to that obtained with conventional vaccine formulations using aluminum hydroxide as the adjuvant. Also, a strong mucosal response is generated, which is not obtained by systemic inoculations of the antigen.

This is the first time that the use of the HBsAg is reported as antigen delivery system through the nasopharyngeal route combined with acemannan. With this system a proportionally increased response was obtained for the epitopes displayed on its surface in relation to the response obtained without using HBsAg as particulating system. This finding allows the formulation of combined vaccines using the HBsAg as an antigen delivery system through the mucous. Different in concept of the carrier activity as T cell bearing molecule capable of enhancing a T cell response against the antigen conjugated. It also supports the use of this strategy for the soluble antigen-particulated antigen combination and its use with polysaccharides with these characteristics through mucosal inoculation routes.

Here, it was generalized that liquid formulations of particulated (non-inactivated, non alive) antigen delivery systems together with the acemannan, inoculated by the nasopharyngeal route, preferentially potentiated the immune response in relation to the soluble antigen until the level of serological response obtained by the systemic route with alum. In the present invention the immunological modulator activity of combined formulations of antigen-acemannan are also described.

At present, the action mechanisms of the acemannan and other immunological stimulators polysaccharides are not completely clear. A possible mechanism could be related with the macrophages and dendritic cells, that have specific receptors for mannose and fucose increasing phagocytosis after antigen entrance. The antigenic assimilation at the nasopharyngeal level and more specifically at the Waldeyer ring—according to the assimilation mechanism for stratified epithelial tissue—can be potentiated with the activation of the macrophages and dendritic cells found in the area and with the attraction toward this zone of an increased number of immunological competent cells.

The particulation of the subunit (non inactivated and non living antigens), through conjugations to particulated antigens or their inclusion or association to delivery systems of antigens, constitutes a first step in antigen processing in this invention, the second step is the addition of the polysaccharide that activates the immune system. Special cases of this invention are those antigens particulated per se. This kind of antigens avoid the use of a particulated antigen delivery system, we have the example of hepatitis B surface antigen and are different to living or inactivated antigens.

The viscous consistency of the acemannan makes it an active vehicle that increases the time of antigen presence at the inoculation site. Other activities as the induction of the cytokines, the activation of mechanisms for antigen uptake by the M cell, the recruitment of different populations of cells from the immunological system and the increase of the antigen presenting activity, are not discarded. But these properties per se are not enough to induce an immune response through the nasopharingeal route.

The formulation, which is the object of this invention, presents, according to the size of the species to be immunized, an amount of inoculum able to cover the nasopharyngeal area up to the subglotis. The dose may be divided in 2 parts for its application or it may be introduced once. The concentration of the polysaccharide used ranged from 1 mg/mL to 9 mg/mL of lyophilized weight corresponding approximately to 0.070–0.600 mg/mL (in total hexose content measured by the antrone method). In spite of this broad range of concentrations, all of them are not capable of inducing optimum responses, at higher doses the responses are affected due to the polysaccharide viscosity, the presence of contaminants from lower molecular weights decrease the acemannan concentration, and the effectiveness of the resulting formulation. The purification method reported permits the higher purity of acemannan and thus its possible to achieve the higher responses. Furthermore this pure polysaccharide will be less reactogenic for humans.

EXAMPLES

Example 1

The acemannan polysaccharide is obtained from the total aqueous extract of the *Aloe barbadensis* Miller leaf. Leaves are collected form plant of 2 to 3 years of age and are stored for 2 to 3 days at 4° C. in a dark room. Later the end and borders of the leaves are eliminated. The leaves are divided in small portions and ground while occasionally adding a minimum amount of sterile water to facilitate the process. The mucilage (or gel found within the leaf) was also used to obtain the acemannan.

The leaves or the gel, after grinding, were centrifuged at 10,000 rpm, eliminating all the insoluble remains that were mainly from the epidermal and fibrous tissues of the leaf. The lyophilized supernatant was named total extract (Te). The Te was resuspended according to convenience for a later 80% ethanol precipitation with slow stirring. Precipitation temperature was of 4° C. After 24 hours the solution was centrifuged for 20 min at 10,000 rpm and the supernatant was discarded. The precipitate was resuspended in sterile distilled water and lyophilized. This product is called ethanol precipitate.

To obtain the acemannan with a high degree of purity, molecular exclusion chromatrography in Sepharose CL-4B was chosen. A phosphate buffer saline solution (PBS) or 0.2 M NaCl was used for the run, as well as for resuspending the sample. FIG. 1 shows the chromatogram of a HPLC chromatography in a filtration gel column TSK G6000PW before the gel filtration in Sepharose CL-4B. In this chromatogram the point corresponding to the elution volume of the Dextran Blue (DB) of MW=2000 kDa is pointed out, and at the end is a point corresponding to the total elution volume (TEV). The first peak (M), of a higher molecular weight than the DB was positive for the Antrone colorimetric method (Trevelyan W. E. y Harrison J. S. 1952 Biochem J. 23: 1824).

The analysis through infra-red spectroscopy of both peaks showed the presence of bands that are characteristic of the acemannan at the first peak of the chromatography (M). These maximums, near 1250 and 1750 $cm^{-1}$, denote the presence of acetylations pertaining to the native state of this polysaccharide. These bands were not observed at the peak corresponding to the total elution volume (TEV) of the column.

Example 2

To determine the immunological potentiator activity of the acemannan through the mucosal route, immunogenicity tests in Balb/c mice of 7 to 10 weeks of age were carried out using the surface antigen model of the hepatitis B virus (HBsAg). The inoculation was carried out through the nasopharyngeal route in volumes of 50 µL in anaesthetized mice. The extraction was carried out by retro-orbital punction at 28 days after the start of the schedule. Titer determination was carried out by anti-total HBsAg ELISA. The statistical analysis was performed by the Student test: $p<0.05$ was considered the significant difference.

Figure 2:
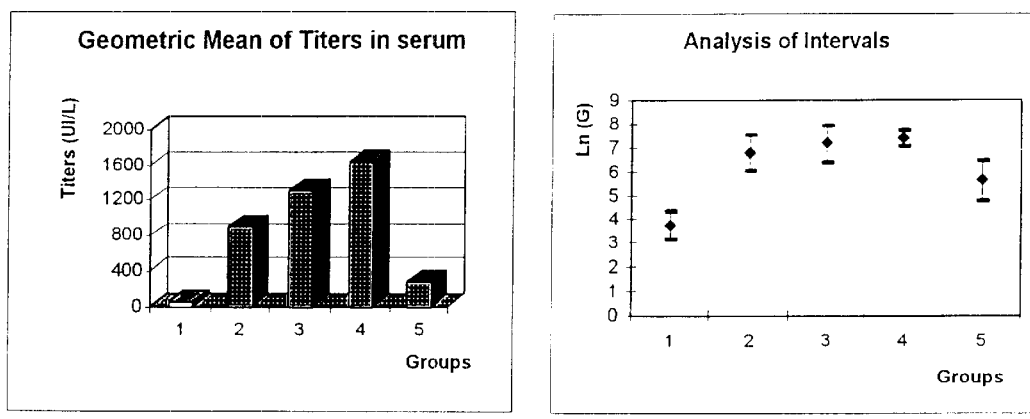
FIG. 2. Response against HBsAg using different acemannan doses.

Different dose levels of the acemannan were tested, the control used was the HBsAg in PBS. The antigen was used in only one level: 5 µg/dosis. Results are shown in the table of FIG. 2.

A strong immunological potentiator activity was evidenced in the groups in which acemannan was added. All groups were significantly superior to the control of HBsAg in PBS. The excesive increase of polysaccharide generated an inhibitory effect (Group 5). This was due to an increase of the resulting viscosity.

Example 3

With the objective of comparing the immunological potentiator activity of acemannan for HBsAg with other reference mucosal adjuvant, an immunization schedule was carried out to compare it with a formulation of HBsAg and the cholera toxin (CT) (FIGS. 3a–d). Several antigen doses were assayed and the systemic inoculation of HBsAg in alum was also used as a control. The schedule was carried out in 8 weeks old Balb/c female mice with four inoculations the days 0, 14, 28 and 56. Extractions were performed the days 26, 42 and 70. The evaluation of the sera was done with the conventional ELISA for the detection of specific mouse IgG antibodies. The sera were analyzed 14 days after the second, third and fourth dose.

Another objective of this assay was to compare the humoral immune response kinetics in the groups involved in the study.

Figure 3A:
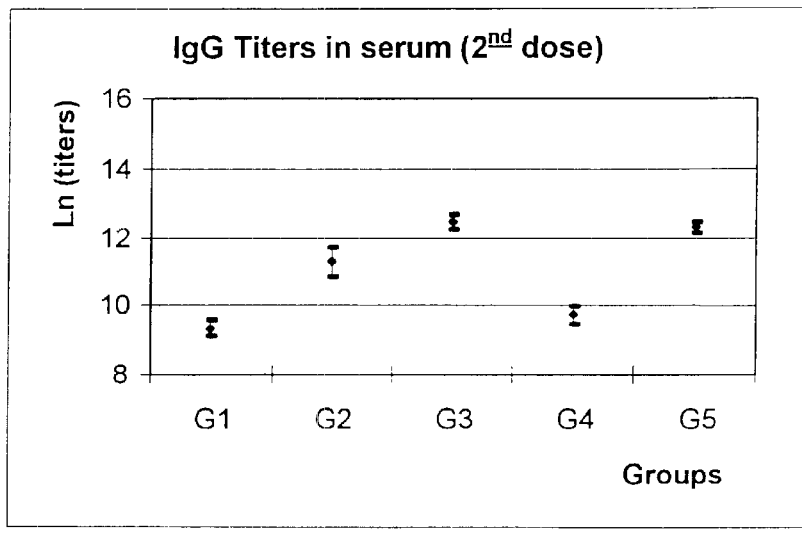
FIG. 3a. Evaluation of sera after the second dose.

A statistical analysis after a second dose did not evidenced significant differences between the alum control group (G4) and the nasal group with the same quantity of antigen (G1). The group of mice immunized with CT as adjuvant by the nasopharyngeal route (G5) generated an antibody response higher than that of the group with the lower quantity of antigen and was not significantly different from that of the group with equal quantity of HBsAg (G2) (FIG. 3a).

Figure 3B:
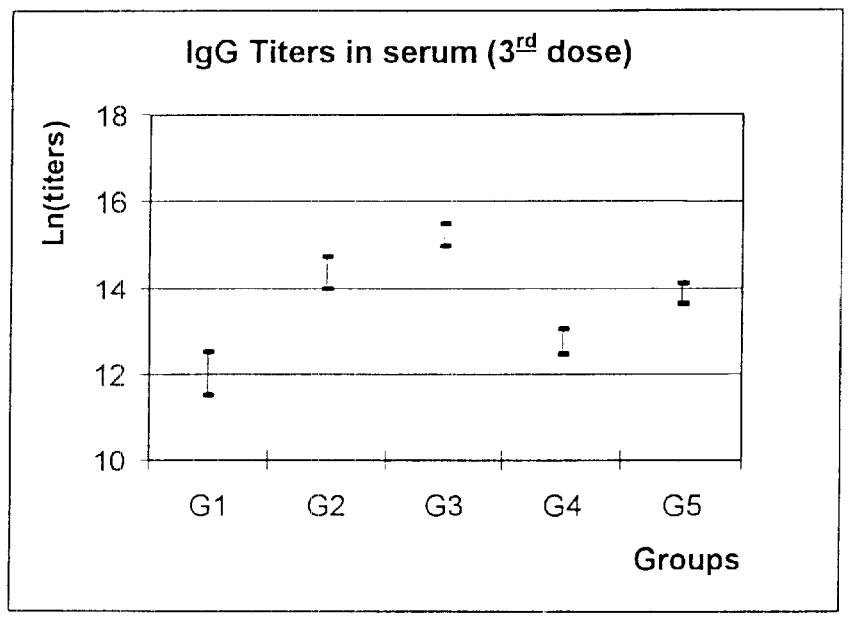
FIG. 3b. Evaluation of sera after the third dose.

After three immunizations, there was no statistical significant difference between the group of mice immunized intranasally and systemically with 2 µg (G1 and G4). In the same way, there was no significant difference between the group of mice immunized with CT as adjuvant (G5) and the equivalent formulation under assay (G2), both with 10 µg of HBsAg (FIG. 3b).

Figure 3C:
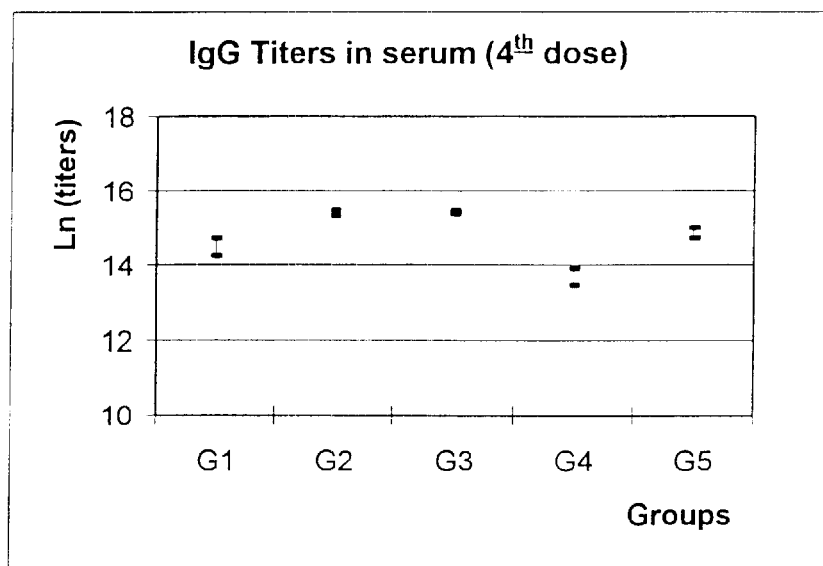
FIG. 3c. Evaluation of sera after the fourth dose.

Having into account the strong increase in titers from the second to the third dose, we undertook the task of proving if this increase followed the same slope for the different groups assayed after a fourth dose, applied one month after the third inoculation. The results are shown in FIG. 3c.

Using acemannan as an adjuvant it is possible to obtain after a fourth dose a response which is higher than that obtained with CT in serum, as evidenced comparing G2 and G5.

The kinetics of the response shows a consistent increase, which after the third and fourth dose exceed the response generated by CT. The antibody levels generated by intranasal inoculation of 2 µg of Ag per dose (G1) were significantly higher to those obtained by the same quantity of antigen administered with alumina by systemic route (G4). This is the first evidence that it is possible to attain through the nasopharyngeal inoculation of subunit recombinant inactive (non inactivated, non alive) particulated antigens, adjuvanted with polysaccharides, responses which are able to exceed in quantity and quality the response generated by systemic inoculations using alumina. Additionally, the fact that a strong mucosal response was only induced by nasopharingeal route, becomes a real possibility the efficient and potentially innocuous human inoculation of HBsAg. This is a special case of particulated antigen of proteoliposomal nature. Other antigens may be used by this route, in order to attain a systemic response of equal strength and higher quality. From this result it may be concluded that other recombinant yeast derived antigens which get particulated, generally with a size similar to HBsAg, could be used with good results by intranasal route.

Quantification in Vaginal IgA (Day 70th)

It is of great importance to attain a mucosal response if it is considered that the sexual is one of the transmission routes of hepatitis B and other diseases.

Figure 3D:
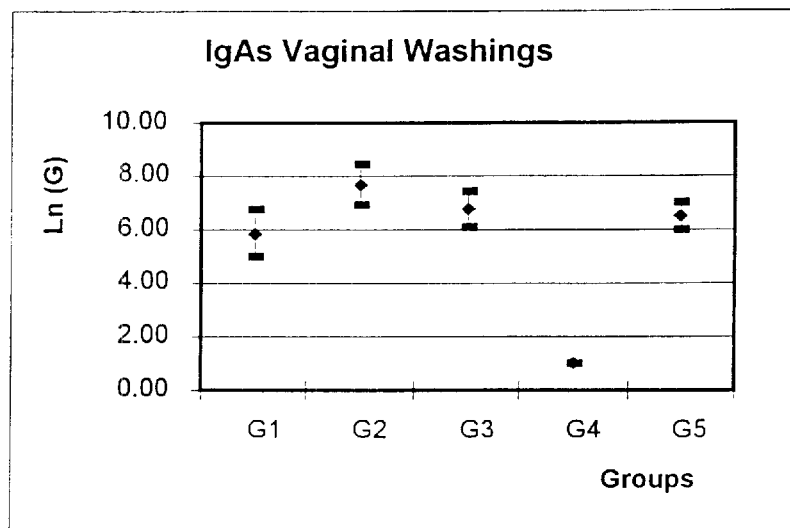
FIG. 3d. Evaluation of the vaginal washings (day 70)

With the objective of comparing the vaginal anti-HBsAg IgA response, vaginal washings were performed with 100 of PBS after 70 days from the first inoculation and the anti-IgA antibody response was analyzed by a conventional ELISA. The results were quantified related to a vaginal washing with a high titer which served as a positive control, therefore relative units (RU) were considered (FIG. 3d).

In the vaginal mucosal secretions of mice immunized with alumina as adjuvant by systemic route (group 4) an anti-HBsAg IgA response was not detected. This result supports the importance of mucosal immunization and specifically the adjuvant's potency, able to generate more strong responses in the groups 2 and 3 even though the response was not statistically significant. The antibody levels attained with 2 µg and the polysaccharide, were not statistically different to those attained with 10 µg and CT.

Example 4

Figure 4:
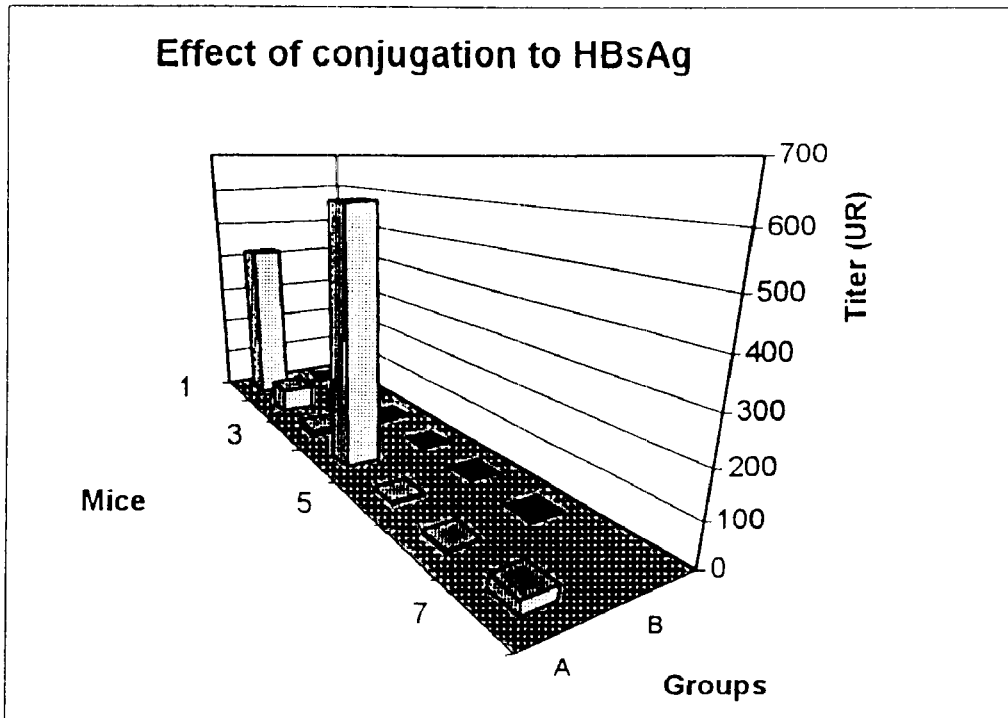
FIG. 4. The schedule used was 0, 14, 28 and the extraction at 42 days. Group A: 20 μg (HBsAg-MAP conjugate mixed with acemannan polysaccharide (6 mg/mL), Group B: 40 μg MAP+acemannan polysaccharide (6 mg/mL).
Figure 5A:
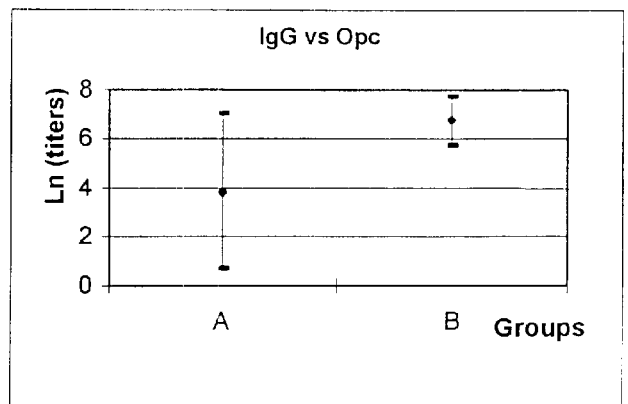
FIG. 5a. Three dose schedule: 0, 28, 56 and extraction at 63 days.
Figure 5B:
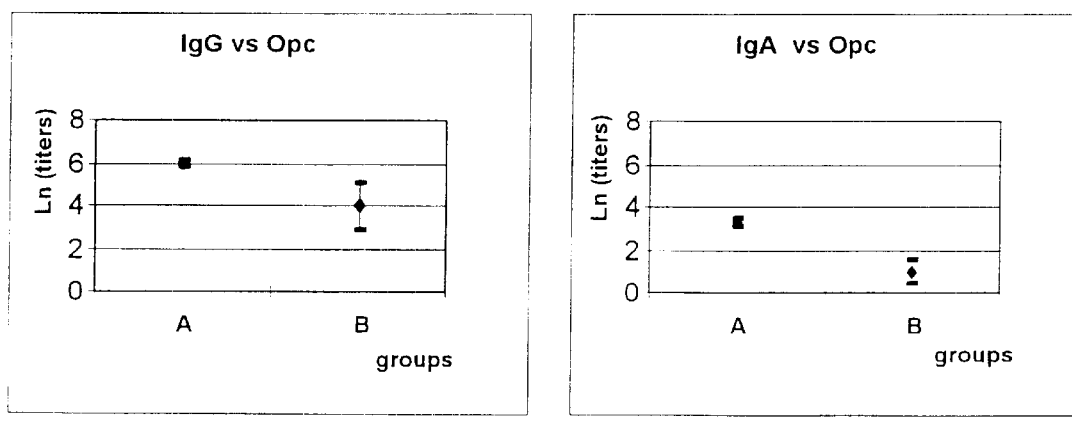
FIG. 5b. Three dose schedule: 0, 28, 56 and extraction at 63 days.

With the objective of demonstrating the possibility of delivering antigens to mucosal tissues HBsAg was used to bind soluble antigens by chemical conjugation to a multi-antigenic peptide (MAP) Th-B, formed by the universal Th epitope (830–843) of the tetanus toxin and a B peptide of the HIV gp 120 V3 loop. The intranasal inoculation was performed as previously described and the blood extraction was also done by retro-orbital puncture 42 days after the schedule was initiated. The determination of the titers was carried out by a B peptide specific anti IgG ELISA. The titers were determined related to a positive control and therefore relative units (RU) were considered (FIG. 4).

In the group B there was no seroconversion. In the group A there was 100% seroconversion, the presence of two high responders mice affects the graphic visibility of the other two which seroconverted but with a lower titer.

Although the MAP (40 μg) was much more represented in the group B regarding to what might be of the same in 20 μg of the HBsAg-MAP conjugate (group A), there was no serum response in the group B. Seroconversion criteria used was twice the average values of the optical densities of negative controls. This result evidenced that particulation more than the presence of Th epitopes plays an important role in the response to the antigen because, having both groups polysaccharide as adjuvant, only the particulated group responsed. This is the first time that HBsAg is selected to be a mucosal delivery system.

As known by the physiology of the inoculation route, particulation is important, but other known mucosal adjuvants such as CT subvert this need. Therefore we may find in the literature numerous examples of immunological potentiating activity of CT for non particulated antigens, among them simple peptides. This effect does not take place with the polysaccharide but with the help of particulation. Subunit non-particulated antigens are not able to be enhanced.

Example 5

The recombinant polypeptide of the Opc protein 5C, one of the *Neisseria meningitidis* outer membrane proteins, was incorporated in liposomes. Its response was evaluated in mice by the nasopharyngeal route by comparing with the response generated by the soluble polypeptide.

Initially the immunological potentiating activity on the liposome was demonstrated. Two groups of 10 Balb/c mice were immunized. The group A was immunized with 20 μg of liposome encapsulated protein and the group B was immunized with 20 μg of the same preparation adding acemannan at a final concentration of 6 mg/mL. The humoral response was evaluated at systemic level and in lung washings.

The IgG levels were measured by ELISA and were represented as logarithms of the arbitrary units assigned to each serum. The group B showed the higher levels of serum IgG, the difference was statistically significant (FIG. 5*a*). This experiment showed the capacity of acemannan to potentiate the immune response to liposomal formulations.

A second experiment was designed to compare the potentiating effect of the polysaccharide on the Opc protein in liposomes (A) and on the renatured Opc protein in octyl-glucoside 10 mg/mL (B). The use of this detergent increased the recognition of the protein by four specific monoclonal antibodies for the natural Opc protein. Two of these antibodies recognize conformational epitopes and the other two lineal epitopes. According to the recognition criteria by monoclonal antibodies, the octyl-glucoside renatured Opc protein presents a conformation closer to the natural protein.

Two groups of 10 Balb/c mice were immunized intranasally. The antibody levels were quantified in the sera and the lung washings and represented as logarithms of the arbitrary units assigned to each sample (FIG. 5*b*).

In serum as well as in the mucosal washings it was observed that the combination of the liposomes with the polysaccharide rendered the higher immunoglobulin titers and the lesser dispersion in the response. The acemannan significantly potentiates the response to the antigen when this is presented to the immune system by the liposome (delivery system for particulated antigens). We can conclude that although the liposomes have been widely used to enhance mucosal responses, it is possible to increase the immune response when they are mixed with acemannan.

What is claimed is:

1. A method for potentiating an immune response to antigens comprising:

administering a formulation comprising a subunit particulated antigen; and acemannan polysaccharide, wherein the administration is by mucosal administration.

2. A method according to claim 1 wherein the mucosal administration is nasopharyngeal administration.

3. A method according to claim 1 wherein acemannan concentration is in the range of 0.070 mg/mL to 0.550 mg/mL of hexose concentration.

4. A method according to claim 1 wherein the subunit particulated antigen is the *Neisseria meningitidis* 5C outer membrane protein.

5. A method according to claim 4, wherein the subunit particulated antigen of *Neisseria meningitidis* 5C outer membrane protein is obtained by adsorption, trapping, covalent linking or electrostatic association to a delivery system.

6. A method according to claim 4, wherein the dose of the 5C antigen is in a range up to 500 μg of protein.

7. A method according to claim 5, wherein the antigen submitted to particulation is a viral, bacterial or uni or multicellular parasite.

8. A method according to claim 5, wherein the antigen is natural, recombinant, or synthetic.

9. A method for potentiating an immune response to antigens comprising:

administering a formulation comprising a subunit particulated recombinant hepatitis B surface antigen; and acemannan polysaccharide, wherein the administration is by mucosal administration.

10. A method according to claim 9 wherein the mucosal administration is nasopharyngeal administration.

11. A method according to claim 9 wherein the dose of hepatitis B surface antigen is between 2 μg and 500 μg.

12. A method according to claim 9 wherein the subunit particulated hepatitis B surface antigen is covalently coupled to soluble antigens.

13. A method according to claim 12 wherein the coupled antigen is a homologous or heterologous antigen and the total antigen dose is between 2 μg and 500 μg of protein.

14. A method according to claim 9 wherein the acemannan is an extract of *Aloe barbadensis* Miller plants wherein the extract has immunopotentiating activity.

15. A method according to claim 9 wherein said response is potentiated in a human or animal.

* * * * *